United States Patent
Avar et al.

[11] Patent Number: 6,153,676
[45] Date of Patent: Nov. 28, 2000

[54] STABILIZED POLYOLEFINS

[75] Inventors: Lajos Avar, Biel-Banken, Switzerland; Gilbert Ligner, Wintzenheim, France; Joseph R. Webster, Charlotte, N.C.

[73] Assignee: Clariant Finance (BVI) Limited, Tortola, Virgin Islands (Br.)

[21] Appl. No.: 09/365,942

[22] Filed: Aug. 2, 1999

Related U.S. Application Data

[63] Continuation of application No. 09/002,806, Jan. 5, 1998, abandoned, which is a continuation-in-part of application No. 08/545,961, Oct. 20, 1995, Pat. No. 5,705,545, which is a continuation-in-part of application No. 08/107,405, Aug. 16, 1993, abandoned, and a continuation-in-part of application No. 08/833,149, Apr. 4, 1997, Pat. No. 5,874,493.

[30] Foreign Application Priority Data

Aug. 17, 1992 [DE] Germany .................. 42 27 216

[51] Int. Cl.⁷ ..................................................... C08K 5/34
[52] U.S. Cl. .............................................. 524/102
[58] Field of Search ............................................ 524/102

[56] References Cited

U.S. PATENT DOCUMENTS

| | | | |
|---|---|---|---|
| 4,110,304 | 8/1978 | Gilg et al. ............... | 252/404 |
| 4,238,613 | 12/1980 | Rasberger et al. ....... | 546/190 |
| 4,876,299 | 10/1989 | Avar .......................... | 524/99 |

*Primary Examiner*—Kriellion Sanders
*Attorney, Agent, or Firm*—Miles B. Dearth; Scott E. Hanf

[57] ABSTRACT

The subject matter of the invention is the use of certain piperidine compounds of formula I

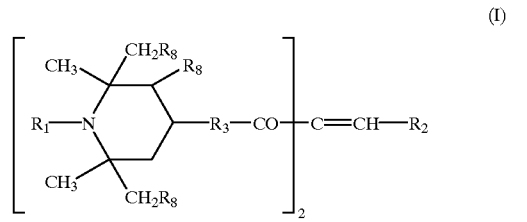

optionally in combination with an oxalanide UV absorber for the stabilization of pigmented or unpigmented polyolefins against the negative consequences of UV radiation. The invention also relates to compositions comprising a piperidine compound of formula I, a polyolefin, and an oxalanide UV absorber and compositions comprising a compound of formula I and a second HALS compound.

1 Claim, No Drawings

STABILIZED POLYOLEFINS

This application is CONTINUATION APPLICATION of Ser. No. 09/002,806 filed Jan. 25, 1998 now abandoned; which is a continuation-in-part of Ser. No. 08/545,961 filed Oct. 20, 1995 (now U.S. Pat. No. 5,705,545); which is a continuation in part of Ser. No. 08/107,405 filed Aug. 16, 1993 (abandoned); which is a continuation in part of Ser. No. 08/833,149 filed Apr. 4, 1997 now U.S. Pat. No. 5,874,493.

The invention relates to polyolefins stabilized with particular hindered amine light stabilizer (HALS) capable of grafting to the polyolefin, and oxalic acid diamide (oxanilide). A surprising synergistic improvement in stabilization of polyolefin against the adverse effects of light has been found.

The subject matter of the invention is thus a composition comprising:
a) a polyolefin;
b) a piperidine compound of formula I (I)

$$\left[ R_1 \underset{R_2\ R_2}{\overset{R_1\ R_9}{N}} A-CO \right]_2 =C=CH-R_{10}$$

in which

R is hydrogen; oxygen; —OH; $C_{1-4}$alkyl; —O—$C_{1-24}$alkyl; —O—CO—$C_{1-24}$alkyl; —O—CO-phenyl or —$COR_3$; where $R_5$ is —$C(R_3)=CH_2$, $C_{1-4}$alkyl, phenyl, CO—$C_{1-24}$alkyl, —CO-phenyl, —$NR_7R_8$, —$CH_2C_4H_3$, —CO—$OC_{1-12}$alkyl or —COOH; where $R_3$ is hydrogen or $C_{1-4}$alkyl; $R_1$ is hydrogen, $C_{1-12}$alkyl, $C_{3-6}$cycloalkyl, phenyl, phenyl-$C_{1-4}$alkyl or $C_{1-4}$alkylphenyl and $R_6$ is $C_{1-12}$alkyl or hydrogen, each $R_1$, independently, is —$CH_3$ or —$CH_2(C_{1-4}$alkyl) or both groups $R_1$ form a group —$(CH_2)_3$; and each $R_2$, independently, is —$CH_3$ or —$CH_2(C_{1-4}$alkyl) or both groups $R_2$ form a group —$(CH_2)_3$.

A is —O— or —N($C_{1-4}$alkyl)— or —NH— (preferably —O—)

$R_9$ is hydrogen or methyl, preferably hydrogen and $R_{10}$ is an aromatic single ring or an aromatic fused 2 or 3 ring group or a heteroaromatic single ring or a heteroaromatic fused 2 or 3 ring group.

Preferably the amount of the compound of formula I added is 0.01–5%, more preferably 0.05 to 2.5% most preferably 0.1 to 0.5% based on the weight of thermoplastic material.

Preferably $R_{10}$ is $R_{10}'$ where $R_{10}'$ is phenyl, unsubstituted or substituted by one to three groups selected from $C_{1-4}$alkyl, $C_{1-4}$alkoxy and —OH or by one or two (preferably two) substituents selected from a group of formula α

$$-CH=O-\left[CO-A-\underset{R_2\ R_2}{\overset{R_9\ R_1\ R_1}{N-R}}\right]_2$$

or $R_{10}'$ is naphthyl or a group selected from groups of formula a–h:

(a) phenyl-O-phenyl (b) phenyl-S-phenyl (c) 2-thienyl (d) benzothiophen-2-yl (e) benzofuran-2-yl (f) fluorenyl (g) 10-($C_{1-4}$alkyl)-phenothiazinyl (h) biphenyl More preferably $R_{10}$ is $R_{10}"$ where $R_{10}"$ is phenyl, unsubstituted or substituted by one to three groups selected from $C_{1-4}$alkyl, $C_{1-4}$alkoxy and OH (maximum one —OH), [especially

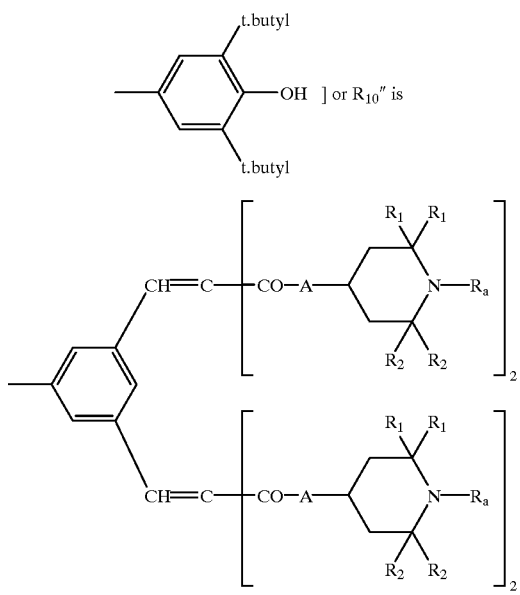

Preferred compounds of formula I are of formula Ia

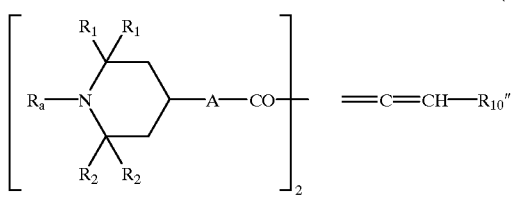

(1a)

where $R_a$ is hydrogen, $C_{1-4}$alkyl, $C_{1-4}$alkoxy, hydroxy or —CO—$R_5'$ where $R_5'$ is —CH=CH$_2$, $C_{1-4}$alkyl or —CO—O—$C_{1-4}$alkyl;

$R_{10}''$ is phenyl, unsubstituted or substituted by one to three groups selected from $C_{1-4}$alkyl, $C_{1-4}$alkoxy and OH (max. one OH) or $R_{10}''$ is a group of formula b)

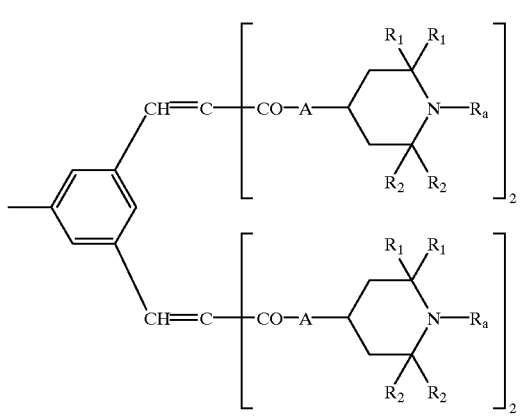

b)

More preferred compound of formula I are of formula Ib

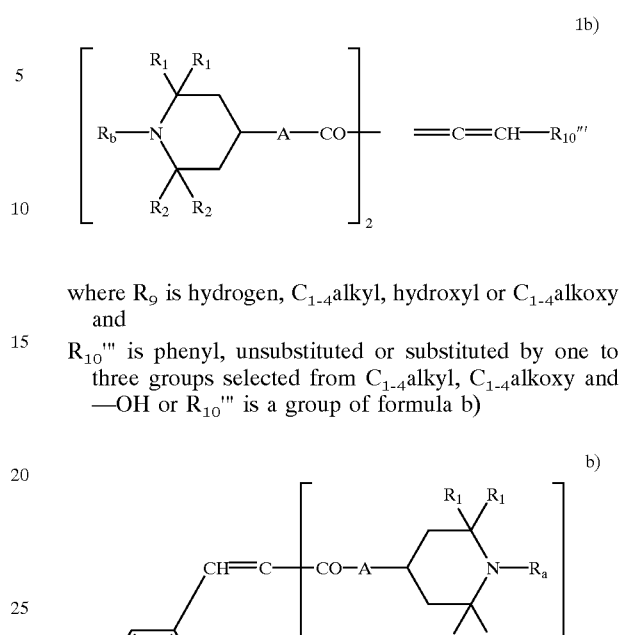

1b)

where $R_9$ is hydrogen, $C_{1-4}$alkyl, hydroxyl or $C_{1-4}$alkoxy and $R_{10}'''$ is phenyl, unsubstituted or substituted by one to three groups selected from $C_{1-4}$alkyl, $C_{1-4}$alkoxy and —OH or $R_{10}'''$ is a group of formula b)

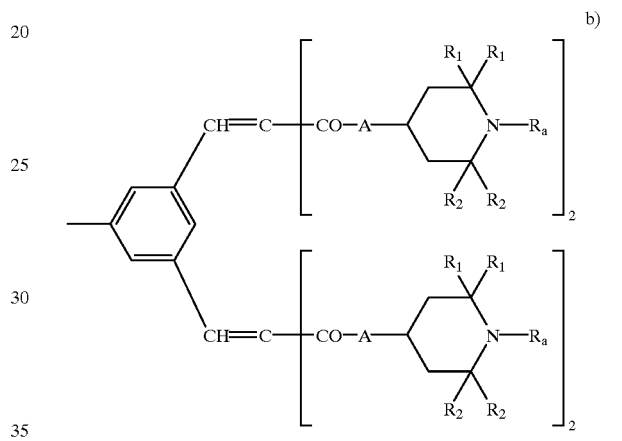

b)

where the symbols are defined above.

Most preferred compounds of formula I are of formula Ic

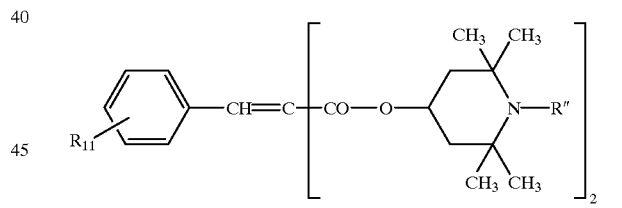

in which $R_{11}$ is $C_{1-4}$alkyl, $C_{1-4}$alkoxy or hydrogen; and

R'' is hydrogen, $C_{1-4}$ alkyl or $C_{1-4}$alkoxy $R_{11}$ is preferably $R_{11}'$ in which $R_{11}'$ is methoxy, ethoxy or hydrogen Most preferably $R_{11}$ is in the 4-position R'' is preferably R''' where R''' is hydrogen, methyl or $C_{1-4}$alkoxy (e.g. methoxy, ethoxy or especially —O—$C_3H_{11}$)

In $R_{10}$, any $C_{1-4}$alkyl groups are preferably $C_{1-4}$alkyl, more preferably methyl or ethyl.

In $R_{10}$ any $C_{1-4}$alkoxy is preferably methoxy, ethoxy or n-acryloxy.

Compounds of formula I are new, with the proviso that when $R_{10}$ is paramethoxyphenyl, R is not hydrogen. Preferably in such new compounds, when $R_{10}$ is alkoxy phenyl, R is not hydrogen. Most preferably in the new compounds of formula I, R is not hydrogen.

Compounds of formula I can be prepared by condensing one mole of a compound of formula II

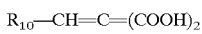

$R_{10}$—CH=C=(COOH)$_2$ (or a derivative thereof e.g. $C_{1-4}$alkyl ester or the acid halide) with 2 moles of a compound of formula III

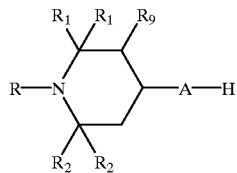

at elevated temperatures (generally 80–200° C.).

Compounds of formula II and III are known or may be made from known compounds by known methods.

A compound of further interest is of formula Id

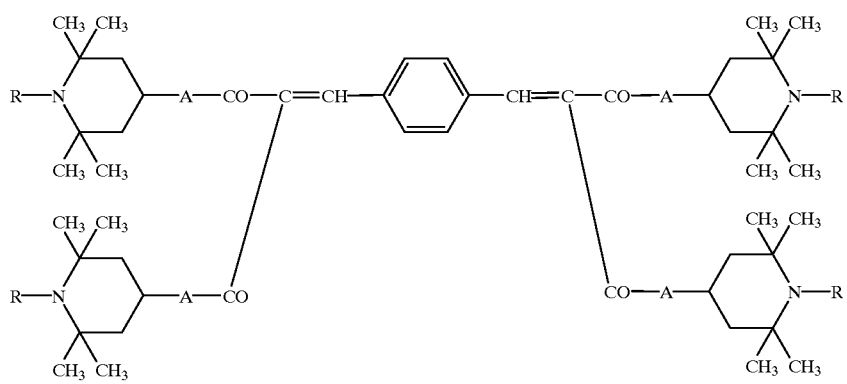

(Id)

The preparation of the compound of formula Id is carried out by reacting one mol of the compound of formula IV

IV

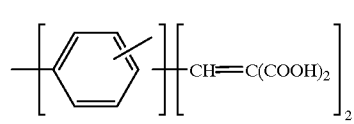

or a derivative thereof with 4 mols of a compound of formula III.

The compounds of formula I are especially suitable for stabilizing polyolefins especially polypropylene, polyethylene (e.g. high density polyethylene, low density polyethylene, linear low density polyethylene or medium density polypropylene) polybutylene, poly-4-methylpentene and of special interest are the α-polyolefins prepared using processing catalysts known as Generation II to Generation V catalysts and which have not been subjected to a catalyst removal step. By the term "catalyst removal step" used herein is meant a step for the purpose of positively removing the catalyst residues contained in the polymerized polyolefins or treating the polyolefins with the compound which can react with the catalyst residue and inactive or solubilize the residue, such as alcohols or water, and then removing the inactivated or solubilized catalyst residue by physical means such as filtration, washing and centrifuging. Thus, in the case of suspension polymerization, the step of separating the resulting polymer from a dispersion medium, such as a solvent or a liquid monomer, does not fall under the above-mentioned definition of the catalyst residue removal step, although the catalyst dissolved in the dispersion medium may be removed by a separation step.

The step of adding a small amount of catalyst portions such as ethers, alcohols, ketones, esters and water to the resulting polymer, to inactivate the catalyst remaining after the completion of polymerization, or the step of treating the resulting polymer suspension with gas such as steam or nitrogen to remove the dispersion medium also does not fall under the above-mentioned definition of the "catalyst residue removal" step.

What we mean by Generation I catalysts are titanium halide catalysts and an organo aluminium compound or an organo aluminium halide.

What we mean by Generation II catalysts are Generation I catalysts supported on an organo magnesium compound or based on an organo chromium compound supported as SiO2.

What we mean by a Generation III catalyst is a Ziegler type complex catalyst supported on a halogen containing magnesium compound.

What we mean by a Generation IV catalyst is a Generation III catalyst with a silane donor.

What we means by Generation V catalysts is a bis-indenyl organo titanium compound supported on alumoxane or bis cyclopentadienyl titanium halides activated by aluminium alkyl compound.

Further generation of highly specific catalysts, especially useful for manufacturing highly stereoregular poly-α-olefins, which are presently under development, belong in the sense of the present invention also to the aforementioned generations of supported catalyst systems. Examples for the microstructure of such highly stereoregular polyolefins are given by syndiotactic polypropylene, isotactic stereoblock polymers, isotactic polypropylene containing stearic defects randomly distributed along the polymer chain (so called anisotactic polypropylene) or stereoregular stereoblock polymers. Due to the rapid progress in the development of never generation catalyst systems the commercial significance of these polymers with novel, highly interesting properties increases more and more. However, residues of such further catalyst generations, as long as they contain metals of the 3d, 4d and 5d series of the periodic system supported analogously to the earlier catalyst generation, can also cause disadvantageous properties in the polymer, as long as such residues are still present in the polymer even if in a deactivated form.

Due to this, it can therefore be expected that the new compositions according to the invention are also suitable for overcoming such disadvantageous properties of the polymer. This means that any disadvantageous interaction between processing stabilizers and the aforementioned residues of catalysts of further generation, particularly the hydrolysis of phosphites and phosphonites, is most effectively inhibited.

These generations of catalysts are described in the Twelfth Annular International Conference on Advances in the stabilization and Controlled Degradation of Polymers held in Luzern, Switzerland, 21–23 May 1990 in an article on pages 181 to 196 inclusive by Rolf Mülhaupe entitled "New Trends in Polyolefin Catalysts and Influence on Polymer Stability". The contents of this article is incorporated herein by reference and especially Table 1 on page 184 describing the Generation of Catalysts:

formula I with a polymeric material or with monomer capable of forming the said polymeric material.

Further according to the invention there is provided a process for reacting a 2,2,6,6-tetraalkyl-piperidinyl compound with (or grafting into) a polymeric material comprising reacting (or grafting) a compound of formula I with a polymer (preferably having one or more unsaturated groups present) or one or more unsaturated monomers capable of reacting with a compound of formula I and exposing this to light.

Preferably such a process catalyzed by U.V. or visible light by exposing the HALS containing polymers or monomeric compositions for up to 500 hours, more preferably for 100–400 hours.

TABLE I

Polyolefin Catalyst Evolution

| Generation | Example | Cat. Act. (g/PP/gTi hatm) | % Act. Ti | Stereoreg. (% insol in heptane) | Process Technology |
|---|---|---|---|---|---|
| I. | TiCl$_4$/AlR$_3$ | 40 | 0.01 | 45% | removal of cat. residues and atactic PP |
|  | TiCl$_3$/AlEt$_1$Cl | 30 | 0.1 | 92% | removal of catalyst residues |
| II | Mg(OEt$_2$)/TiCl$_1$/AlR$_3$ | 40000 |  | 50% | no removal of cat. residues |
|  | SiO$_2$/Cp$_2$Cr | 40000 | HDPE |  | (mainly HDPE/LLDPE) |
| III | Mod. TiCl$_3$ cat. | 5000 | 1 | 95% | no purification |
|  | MgCl$_3$/TiCl$_1$/AlR$_3$ -ester donor | 20000 | 10 | 92% |  |
| IV | MgCl$_2$/TiCl$_1$AlR$_3$ -silane donor | 40000 | 18 | 99% | no purification no extrusion |
| V | Bis-indenyl-TiR$_1$ on AlCH$_3$O)$_2$ | 40000 | 100 | 99% | novel PPs$_1$ narrow MWD |

In which R, in Table 1, is an organo group; HDPE is high density polyethylene, LLDPE is linear low density polyethyene, Cp is cyclopentadienyl, Et is ethyl, PP is polypropylene and MWD is molecular weight distribution.

Further additives that can be added to a composition according to the invention include antioxidants, such as sterically hindered phenols, secondary aromatic amines or thioethers, such as described in "Kunststoff-Additive" Gächrer/Miller, Ed. 3, 1990 p. 42–50, the contents of which are incorporated herein by reference; acid scavengers such as sodium, magnesium or calcium stearates or lactates, hydrotalcite or alkoxylated amines; U.V. stabilizers such as sterically hindered amines (for example N-unsubstituted, N-alkyl or N-acyl substituted 2,2,6,6-tetra-methylpiperidine compounds) [also known as hindered amine light stabilizers -HALS] and U.V. absorbers (e.g. 2-(2'-hydroxyphenyl)-benztriazoles, 2-hydroxy-benzophenones, 1,3-bis-(2'-hydroxybenzyl) benzene salicylates, cinnamates and oxalic acid diamides;), U.V. quenchers such as benzoates and substituted benzoates, antistatic agents, flameproofing agents, lubricants, plasticisers, nucleating agents, metal deactivators, biocides, impact modifiers, fillers, pigments and fungicides.

The compounds of formula I when added to polymeric material (preferably material having one or more unsaturated groups present) have been found to react or graft either totally or at least in part to the polymeric material (especially plastic material) and generally only react in the present of U.V. light. This is especially true when the polymeric material is a polyolefin.

Still further, therefore according to the invention there is provided a polymeric material containing a 2,2,6,6-tetraalkylpiperidinyl group derived from a compound of formula I that has been reacted with or grafted into the polymeric material. By the term "derived" is meant that group that results from the reaction of a compound of The polymeric material can further be stabilized by adding a phenolic antioxidant. In such a case from 0.01 to 0.2% (especially about 0.1%) of phenolic antioxidant based on the weight of polymeric material is added. Examples of such phenolic antioxidants are Irganox 1010

A further additive that can be added to calcium stearate. This is preferably added in an amount of 0.01 to 0.2% especially 0.1% based on the weight of polymer in the polymeric material.

The compounds of formula I may be added during polymer formation by adding it to the monomeric material from which the polymeric material can be formed. It may also, however, be added to the polymeric material when it is being made up into a coating material (e.g. during coating lacquer formations)

Polyolefin especially polypropylene is the preferred polymeric material to which the compounds of formula I may be added. In such a case, the compounds of formula I can be mixed with powdered polymeric material, melted and then worked in formed articles (e.g. fibers, threads, films bands on thin plates) in which the grafting reaction may be performed by exposure to visible light or light in the near U.V.

Polymer articles of large size can also be formed from a polymeric material with which a 2,2,6,6-tetraalkylpiperidinyl compound derived from a monomer of formula I The polymeric substrate (e.g. polypropylene) can contain other stabilizers especially light stabilizers e.g. U.V. absorber radical scavengers (e.g. HALS). Examples of such stabilizers are oxalanilides, benzotriazoles, 2-hydroxybenzophenones, 2-hydroxyphenyl-s-triazines and HALS such as Tinuvin 770, Tinuvin 944 or Tinuvin 946.

Another embodiment of the invention is a composition comprising b) and c), as defined above, in the range of ratios (wt./wt.) of 4:1 to 1:4, especially 3:1, 2:1, 1:1, 1:2, and 1:3. These compositions may also comprise one or more additional HALS compounds, UV absorbers, primary and secondary antioxidants, and antacids (i.e., acid acceptors).

Another embodiment of the invention is a composition comprising a piperidine compound of formula I and a second HALS compound in the range of ratios (wt./wt.) of 3:1 to 1:3, especially 2:1, 1:1, and 1:2. Said second HALS include commercially available products such as Tinuvin 123 and 622, Chimassorb 944 and 119, HA88, and Uvisil 299 and 2000.

The following compounds of formula Ia are preferred

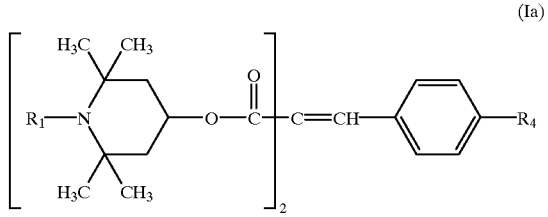

(Ia)

wherein $R_1$ is H, $CH_3$, $OC_8H_{17}$, $C(O)CH_3$, or p-$C_{1-8}$alkoxy-substituted benzene; and $R_4$ is H or $OCH_3$ The compounds of formula I may be prepared by methods taught in DE 3,412,227 and U.S. Pat. No. 5,705,545 which are hereby incorporated by reference as if disclosed herein.

The polyolefins are preferably polypropylene, polyethylene, and copolymers thereof. The polypropylene is preferably polypropylene fiber and thick section polypropylene.

Polypropylene fiber means the unit that forms the basic element of fabrics and other textile structures and Is characterized by having a length at least 50 times its diameter or width. The term, as used herein. Includes fibers; yarns, slit tapes, and fabrics. Thick section polypropylene means a polypropylene article having a thickness or diameter of at least 20 mils or from 600 to greater than 1000 microns.

"Low molecular weight alkyl" means groups with 1 to 8, especially 1 or 2, carbon atoms, "Acyl" means the radicals of formic, acetic, or propionic acid.

The mono- or binuclear aromatic group $R_2$ are, e.g., benzene, naphthalene, and nitrogen and/or sulphur containing five- or six-membered rings, which are optionally anellated to a benzene ring, and which bear, e.g., a sterically hindered hydroxyl as a substituent (3,5-ditert-butyl-4-hydroxyphenyl), or a thienyl group. Aromatic six-membered rings are preferred. The substituents which may be present on these rings are, e.g., hydroxyl, low molecular weight alkyl or alkoxy, preferably methyl, tert.-butyl, methoxy, ethoxy, hydroxyl, and one or two groups of formula

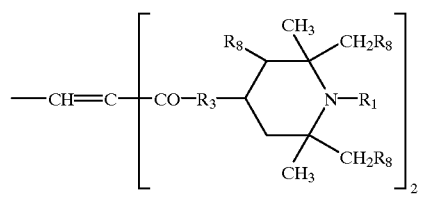

In addition to the piperidine compounds of formula I and the oxalanide UV absorber, in one embodiment of the invention further commercial additives may be additionally employed in the polyolefin substrates, such as primary or-secondary anti-oxidants or mixtures thereof, secondary aromatic amines, thioethers, phosphorus compounds, biocides, metal deactivators, further HALS compounds, further UV absorbers, anti-static agents, and the like, as well as various finishing assistants or Inert filler materials, e.g. talcum, mica, $TiO_2$, chalk, glass, barite, acid acceptors (antacids) etc.

The metal deactivators include commercially available compounds such as Irganox 1024 and Naugard XL-1.

The UV absorbers include hydroxy-substituted benzophenones such as Cyasorb UV 9, 24, 207, 284, 416, 531, and 2126; Uvinul 3000, 3008, 3040, 3049, 3050, and 3060; hydroxy-substituted benzotriazoles such as Cyasorb 5411 and Tinuvin 234, 326, 327, 328, 384, 900, and 1130; triazines such as Cyasorb 1164 and 1164(L), Tinuvin 1577, and Uvinul T-150; salicylic acid ester; formamidine; cyanoacrylates such as Uvinul 3038 and 3039; and benzyldenmalonate esters such as Cyasorb 1988.

The acid acceptors include metallic oxides and stearates and MgAlOH carbonates.

Finished articles stabilized according to the invention are superior to articles according to the prior art In respect of their substantially longer period of use.

The compound of formula I (b) and the UV absorber (c) or a composition comprising (b) and (c) may be added to the pigmented or unpigmented polyolefin substrate before, during or, after the manufacture thereof. Pigments are intended to include all organic and inorganic (e.g., Ultramarine Blue, $TiO_2$) pigments.

The concentration of the piperidine compound of formula I is 0.01 to 2% by weight, preferably 0.1 to 1%, based on polyolefin a). The concentration of UV absorber c) is 0.01 to 1% by weight, preferably 0.05 to 1%, most preferably 0.1 to 0.6%, based on polyolefin a). The concentration of a composition comprising a piperidine compound of formula I and a second HALS compound in the range of ratios of 3:1 to 1:3 is 0.01 to 1% by weight, based on polyolefin a). The addition of the pigmentation to polyolefin may be effected in accordance with generally conventional processes in pure form as so-called full pigments, in pre-dispersed form as concentrates, masterbatches and the like, or in combination with further admixtures.

A further object of the Invention Is a process for the stabilization of pigmented or unpigmented polyolefins against the negative consequences of light which comprises adding to said polyolefins a quantity sufficient for stabilization of at least one piperidine compound of formula I and an oxalanide UV absorber c).

In the following examples which illustrate the invention, the parts and percentages are by weight, and the degrees are degrees celsius.

EXAMPLE 1

UV Stability

To test the stability of polypropylene treated with the composition of the invention against the adverse effects of UV radiation, tests were conducted on 600/34 natural yarns (18 dpf) treated as follows:

A melt compounded masterbatch of 10% (wt.) HALS (either one or a combination of HALS) was prepared and let down into a 8 MF (melt flow in g/10 minutes) polypropylene homopolymer and melt compounded (i.e., extrusion compounded) at 216–221° C. into pelletized form. The pelletized resin contained either HALS alone or in combination with UVA. An appropriate amount of pelletized resin was melt extruded into 18 dpf fibers at 265° C. to yield the various concentrations of test materials and prepared into fabric.

The compounds used were:

| | |
|---|---|
| HALS 1 is | Chimassorb 944, poly[[β-[1,1,3,3-tetramethyl butyl)amino]-s-triazine-2,4-diyl][[2,2,6,6-tetramethyl-4-piperidyl)imino]hexamethylene [(2,2,6,6,-tetramethyl-4-piperidyl)imino]] |
| HALS 2 is | Chimassor 119, 1,3,5-triazine-2,4,6-triamine, N,N'''-[1,2-ethanediylbis[[[4.6-bis[butyl (1,2,2,6,6-pentamethyl-4-piperidinyl)amino]-1,3,5-triazine-2-yl]imino]-3,1 propanedyl]]-bis[N',N''-dibutyl-N',N''-bis(1,2,2,6,6-pentamethyl-4-piperidinyl)- |
| HALS 3 is | Tinuvin 123, bis-(1-octyloxy-2,2,6,6,tetra-methyl-4-piperidinyl)sebacate |
| Sanduvor® PR-31 is | a compound of the formula Ia where $R_1$ is —OCH$_3$ and $R_4$ is methyl, propanedioic acid, [(4-methoxyphenyl)-methylene]-bis(1,2,2,6,6-pentamethyl-4-piperidinyl)ester |
| UVA1 is | Ferro AM 340, benzoic acid, 3,5-bis(1,1-dimethylethyl)-4-hydroxy-, 2,4-bis(1,1-dimethylethyl)phenyl ester |
| UVA2 is | Tinuvin 234, 2-(2H-benzotriazol-2-yl)-4,6-bis(1-methyl-1-phenylethyl)phenol |
| Sanduvor® VSU is | 2-ethyl-2'-ethoxy-oxalanilide |

The tests were run using test standard SAE J 1885 at 89° C. and a high temperature xenon lamp. Test results are in KJ/m² to degradation. The data demonstrate that PR-31 alone (test 3) or in combination with another HALS compound, especially an aminoether type HALS such as Tinuvin 123, enhances polypropylene stability against the degradation by UV light when compared to combinations of other HALS compounds (e.g., compare tests 5 and 6) and that PR-31 also enhances this stability when used in combination with a UV absorber (e.g., compare tests 9 and 10), the best of which absorbers Is Sanduvor® VSU (e.g., compare tests 12, 13, and 14).

®Sanduvor is a registered trademark of Sandoz Ltd.

EXAMPLE 2

Pigmented Fiber

To test the stability of pigmented polypropylene with the compositions of the invention, an 8 dpf automotive fiber was prepared pigmented with 1.0% to $TiO_2$. The tests were run using test standard Amoco Fabrics & Fibers Internal Scratch Test Method. Test results (HTX) are in hours to failure.

TABLE 2-1

| Test | HALS 0.72% | UVA 0.36% | HTX |
|---|---|---|---|
| 1 | PR-31 | VSU | 3853 |
| 2 | HALS2 | UVA2 | 2594 |

We claim:

1. Polyolefin containing a hindered amine compound according to (1)

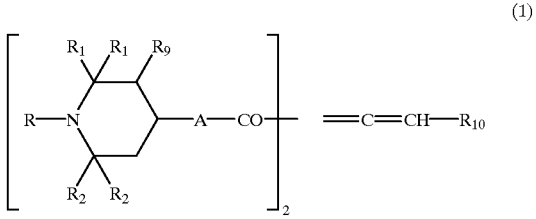

(1)

wherein R is selected from the group consisting of oxygen, —OH, $C_{2-24}$ alkyl, —O—$C_{1-24}$ alkyl, —O—CO-phenyl and $COR_5$, where $R_5$ is —C($R_3$)=$CH_2$, $C_{1-6}$ alkyl, phenyl CO—$C_{1-24}$ alkyl, —CO-phenyl, —NR$_7$R$_8$, —$CH_2$—$C_6H_5$, —CO—O$C_{1-12}$ alkyl or —COOH, where $R_3$ is hydrogen or $C_{1-4}$alkyl; $R_7$ is hydrogen, $C_{1-12}$ alkyl, $C_{5-6}$cycloalkyl, phenyl, phenyl-$C_{1-4}$ alkyl, or $C_{1-12}$ alkylphenyl and $R_8$ is $C_{1-12}$ alkyl or hydrogen;

each $R_1$ and $R_2$ are, independently, —$CH_3$, or —$CH_2(C_{1-4}$ alkyl) or both $R_1$ or both $R_2$ form a group —$(CH_2)_5$—;

A is —O—, —N($C_{1-4}$ alkyl), or —NH—

$R_9$ is hydrogen or methyl, $R_{10}$ is unsubstituted phenyl, napthyl, a nitrogen-, oxygen- or sulfur-containing five- or six-membered ring which is optionally annellated to one or two benzene rings, or $R_{10}$ is substituted phenyl containing one to three groups

TABLE 1-1

| | % Additive Used | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| HALS 1 | 0.6 | | | | | | | | | | | | | | | |
| HALS 2 | | 0.6 | | | 0.3 | | 0.3 | | 0.3 | | 0.3 | | 0.3 | | 0.6 | |
| HALS 3 | | | | 0.6 | 0.3 | 0.3 | | | | | | | | | | |
| Sanduvor PR-31 | | | 0.6 | | | 0.3 | | 0.3 | | 0.3 | | 0.3 | | 0.3 | | 0.6 |
| UVA 1 | | | | | | | 0.3 | 0.3 | | | | | | | | |
| UVA 2 | | | | | | | | | | | | | 0.3 | 0.3 | | |
| Sanduvor VSU | | | | | | | | | | | 0.3 | 0.3 | | | 0.3 | 0.3 |
| Results | 902.4 | 1353.6 | 1466.4 | 1128 | 1240.8 | 1579.2 | 676.8 | 1466.4 | 564 | 1240.8 | 902.4 | 1804.8 | 564 | 1466.4 | 564 | 2594.4 | selected from the group consisting of $C_{1-8}$ alkyl, —OH, $C_{1-8}$ alkoxy other than methoxy, at least one substituent of the formula (α)
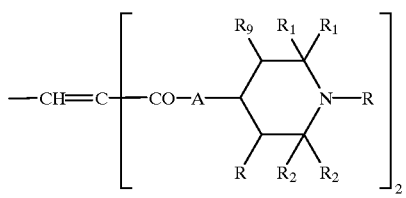
or $R_{10}$ has the formula (a), (b), (c), or (d)
(a)
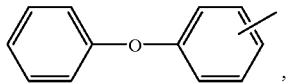
(b)
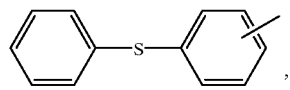
(c)
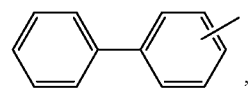
(d)
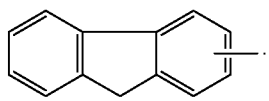
* * * * *